United States Patent [19]

Purvis et al.

[11] Patent Number: 5,376,070
[45] Date of Patent: Dec. 27, 1994

[54] DATA TRANSFER SYSTEM FOR AN INFUSION PUMP

[75] Inventors: Richard E. Purvis, Pasadena; Fredric C. Colman, Granada Hills, both of Calif.

[73] Assignee: MiniMed Inc., Sylmar, Calif.

[21] Appl. No.: 952,930

[22] Filed: Sep. 29, 1992

[51] Int. Cl.⁵ .............................................. A61M 1/00
[52] U.S. Cl. ........................................ 604/31; 604/65; 604/67
[58] Field of Search .................................. 604/65–67, 604/31; 607/32, 60

[56] References Cited

U.S. PATENT DOCUMENTS

| | | | |
|---|---|---|---|
| 4,498,843 | 2/1985 | Schneider et al. | 604/65 |
| 4,790,816 | 12/1988 | Sundblom et al. | 604/31 |
| 4,857,050 | 8/1989 | Lentz et al. | 604/67 |
| 5,087,245 | 2/1992 | Doan | 604/67 |
| 5,101,814 | 4/1992 | Palti | 604/31 |
| 5,117,825 | 6/1992 | Grevious | 607/60 |

*Primary Examiner*—Jerome L. Kruter
*Attorney, Agent, or Firm*—Kelly Bauersfeld & Lowry

[57] ABSTRACT

A data transfer system is provided for communication with an infusion pump of the type used for programmable delivery of medication such as insulin to a patient. The data transfer system includes a communication station having a shaped pocket formed therein for seated reception of the infusion pump. Optical communication members including light emitting and detecting devices mounted on the pump and station are aligned for two-way data transmission when the pump is seated within the station pocket. The communication station can be used directly to monitor data received from the pump, and to transmit reprogrammed data to the pump, as desired. Alternately, the communication station can provide a data relay link to a remote site such as to a computer via a computer data cable, or a modem.

21 Claims, 2 Drawing Sheets

DATA TRANSFER SYSTEM FOR AN INFUSION PUMP

BACKGROUND OF THE INVENTION

1. Field of the Invention

The present invention relates generally to improvements in infusion pumps of the type used for controlled, preprogrammed delivery of medication to a patient, and more particularly to a data transfer system designed for two-way communication with a programmable infusion pump in a manner which facilitates monitoring of pump operation, and/or permits convenient pump reprogramming from a remote location, if desired.

Infusion pump devices and systems are generally known in the medical arts, for use in delivering or dispensing a prescribed medication to a patient. In one form, such devices comprise a relatively compact pump housing adapted to receive a syringe carrying a prescribed medication such as insulin for administration to a patient through infusion tubing and an associated catheter or the like. The infusion pump operates a small drive motor connected to a syringe piston plunger to administer the medication to the patient.

Programmable control means are normally provided for operating the drive motor continuously, or at periodic intervals, to obtain a closely controlled and accurate delivery of medication over an extended time period. Such infusion pumps are utilized to administer insulin and other medications, with an exemplary pump construction being shown and described in U.S. Pat. No. 4,562,751, to Nason et al.; in U.S. Pat. No. 4,678,408, to Nason et al.; and in U.S. Pat. No. 4,685,903, to Cable et al. All three of these patents are assigned to the assignee of the present application.

The infusion pump commonly includes a plurality of externally accessible control buttons or the like, which are manipulated in relation to a visual display to program the pump in accordance with patient medication requirements. Initial pump programming is normally performed by the patient's physician or by other medical personnel. However, particularly in the case of infusion pumps used to administer insulin to diabetic patients, the control buttons and related pump control circuitry are designed to accommodate at least some patient intervention to vary medication delivery times and doses in accordance with actual patient requirements.

In this regard, many modern programmable infusion pumps also include internal memory means for generating and storing data representing actual pump operation over a period of time. The stored data may be reviewed on a periodic basis by medical personnel, so that the patient's condition and treatment regimen can be closely monitored, and the pump reprogrammed as needed. Unfortunately, data retrieval from the pump and/or physician-dictated modification of the basic pump program have required regular patient visits to a medical treatment facility.

The present invention relates to a relatively simple and effective data transfer system designed for retrieving data from, and sending program data to, a medication infusion pump. The data transfer system is particularly suited for remote monitoring and/or reprogramming of the infusion pump.

SUMMARY OF THE INVENTION

The disadvantages and limitations of the background art discussed above are overcome by the present invention. With this invention, a data transfer system is provided for use with a medication infusion pump of the type having programmable control means for scheduled delivery of a selected medication to a patient. The data transfer system comprises a compact communication station having a shaped cradle or pocket for seated reception of the infusion pump.

In the preferred embodiment, optical communication means on the pump and the station are aligned with each other for two-way data transmission when the pump is seated within the station pocket. The communication station includes control means to permit monitoring of retrieved data, and/or transmission of reprogramming data to the pump. Alternately, the communication station may comprise a relay link for transmitting data between the pump and a remote site, such as to a computer, by means of a computer data cable or modem.

In the preferred form, the optical communication means comprises a light emitting device and a light detecting device mounted in pairs on both of the infusion pump and the communication station. The positions of these optical devices are selected for close alignment of the light emitting device on the pump with the light detecting device on the station, and vice versa, when the pump is seated within the station pocket. A station controller operated by key switches or the like on the station permit appropriate two-way data communication via the optical interface.

Data retrieved from the infusion pump may be monitored directly at the communication station, such as by display on a station monitor. Similarly, the station key switches can be manipulated to send appropriate reprogramming data to the pump. Alternately, the station may be equipped with a computer cable port for use in connecting a computer into communication with the pump. Still further, the station may include a phone jack operable in association with an internal modem to permit phone-line communication with a remote computer.

Other features and advantages of the present invention will become more apparent from the following detailed description, taken in conjunction with the accompanying drawings which illustrate, by way of example, the principles of the invention.

BRIEF DESCRIPTION OF THE DRAWINGS

These and other advantages of the present invention are best understood with reference to the drawings, in which:

FIG. 5 is an enlarged fragmented and generally schematic diagram illustrating an optical data transfer interface between the infusion pump and communication station.

DETAILED DESCRIPTION OF THE PREFERRED EMBODIMENT

Figure 1:
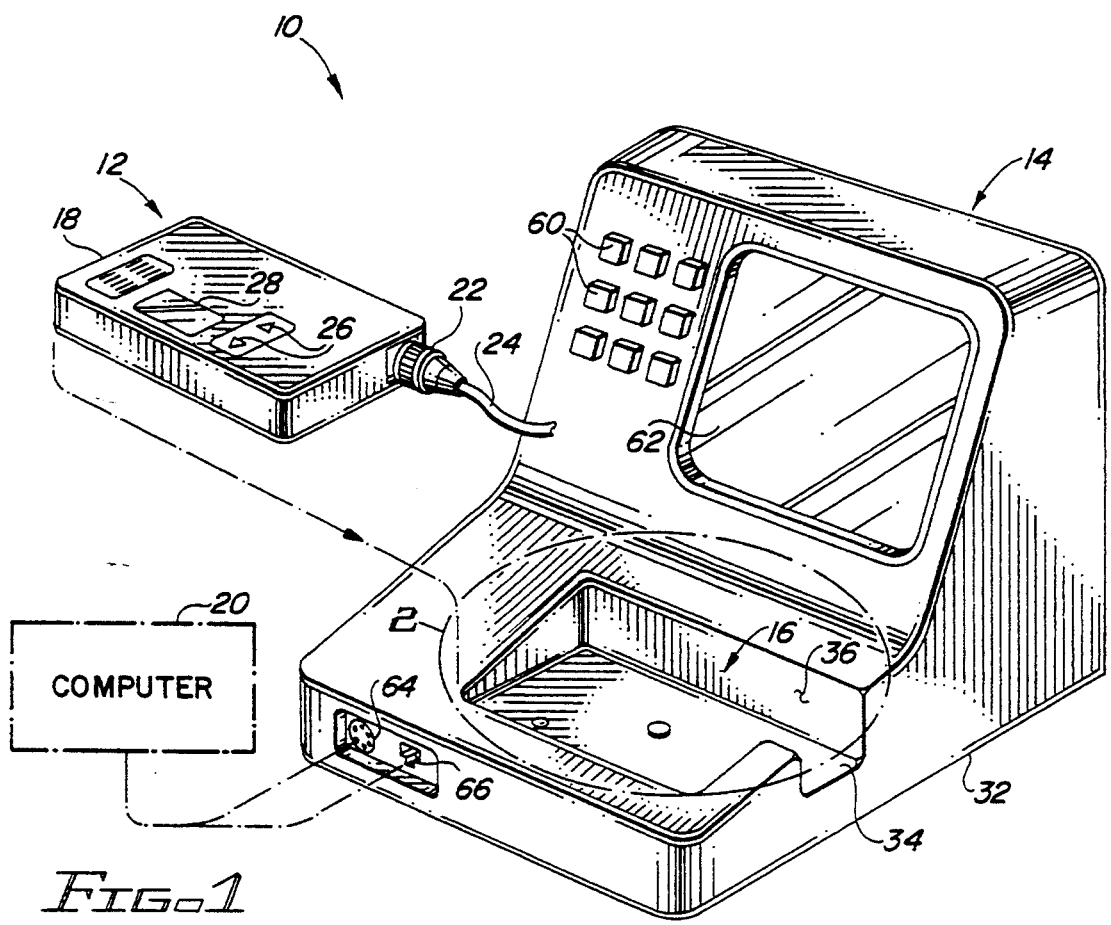
FIG. 1 is an exploded perspective view illustrating a data transfer system embodying the novel features of the present invention, for use in retrieving and sending data with respect to a small, handheld medication infusion pump.

As shown in the exemplary drawings, a data transfer system referred to generally in FIG. 1 by the reference numeral 10 is provided for retrieving data from and sending data to an infusion pump 12 of the type used for controlled or preprogrammed administration of medication to a patient. The data transfer system 10 comprises a compact communication station 14 having a shaped cradle or pocket 16 for seated reception of the infusion pump 12. An optical communication interface, including aligned optoelectronic components on the pump 12 and station 14, provides for two-way data transfer.

The data transfer system 10 of the present invention is particularly designed for quick and easy communication with a medication infusion pump 12, for purposes of monitoring a patient treatment regimen and/or altering the programmed operation of the pump in accordance with individual patient needs.

The communication station 14 receives and supports the infusion pump 12 for data exchange therewith, all in a manner which does not interrupt normal pump operation and further in a manner which does not require any access to or exposure of the interior of a typically waterproof or water resistant pump case 18. The communication station 14 may be used directly for monitoring and/or reprogramming pump operation, or alternately as a data relay link for facilitated data exchange with a remote computer 20.

Figure 4:
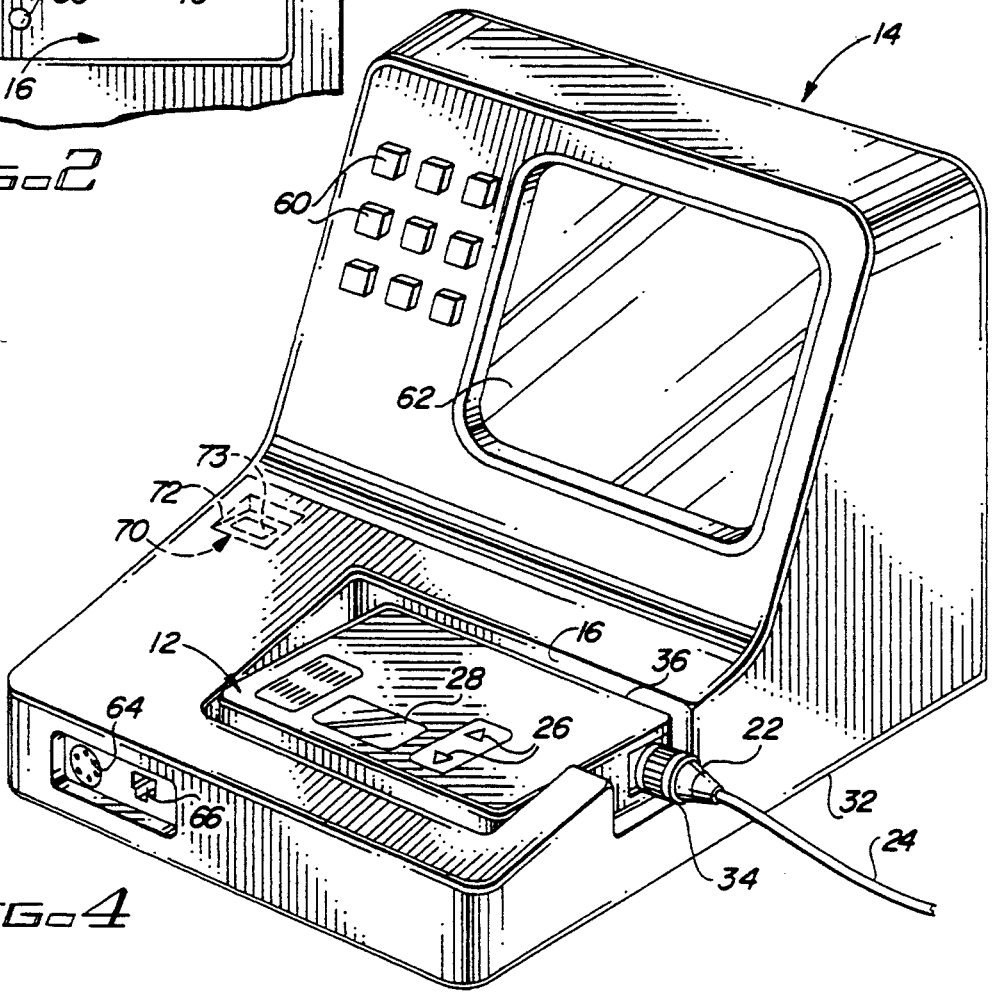
FIG. 4 is a perspective view similar to FIG. 1, but illustrating the infusion pump seated within a shaped pocket defined by a communication station.
Figure 3:
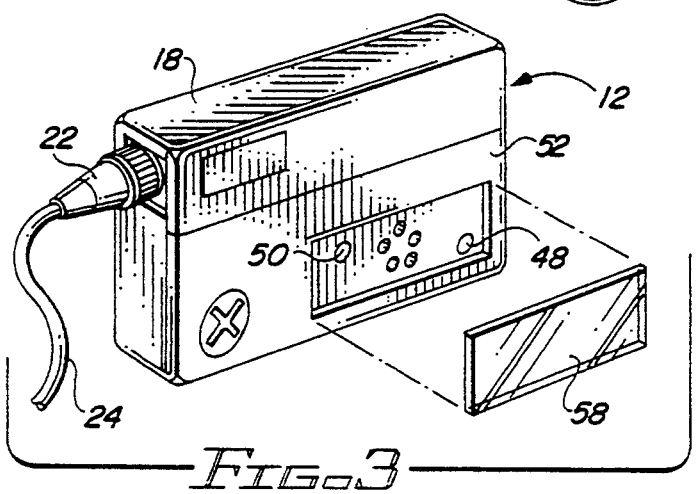
FIG. 3 is an enlarged exploded rear perspective view depicting the infusion pump for use in the data transfer system.

The infusion pump 12 illustrated in FIGS. 1, 3 and 4 has an overall construction and operation which is generally known in the art. More specifically, the infusion pump 12 includes a relatively compact pump case 18 adapted to receive and support a syringe (not shown) charged with a selected medication, such as insulin, to be administered to a patient. The medication-containing syringe carries a luer fitting 22 which protrudes outwardly from one side of the pump case 18 for suitable connection with an infusion line 24 through which the medication is delivered to a patient, typically via a catheter (not shown).

The pump includes an externally exposed array of actuator key switches or buttons 26 or the like in association with a display panel 28 for use in operating and/or programming an internal pump controller 30 (FIG. 5). Infusion pumps of this general type are depicted in U.S. Pat. No. 4,562,751, to Nason, et al.; in U.S. Pat. No. 4,678,408, to Nason, et al.; and in U.S. Pat. No. 4,685,903, to Cable, et al., All three of which are assigned to the assignee of the present invention and are hereby incorporated herein by reference.

Figure 2:
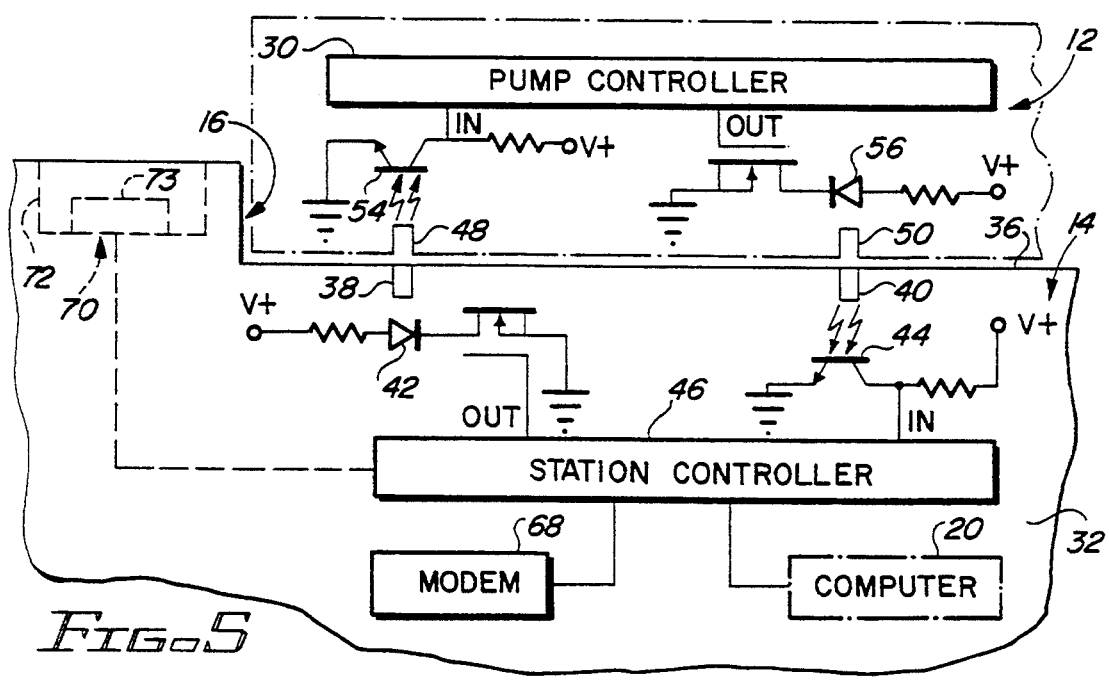
FIG. 2 is an enlarged fragmented plan view corresponding generally with the encircled region 2—2 in FIG. 1.
Figure 2:
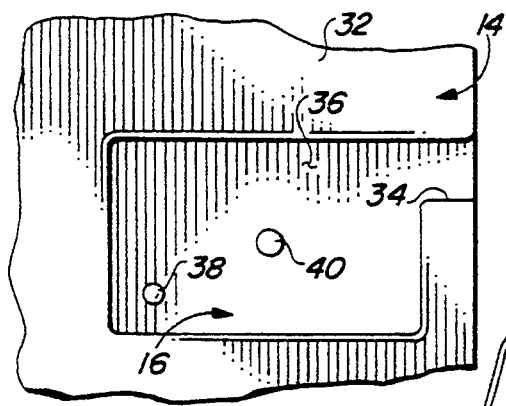

The communication station 14, in the preferred form, has a compact size and shape for convenient desktop use. The contoured pocket 16 is formed in a convenient, externally accessible position on a station housing 32, wherein the pocket 16 has a distinctive size and shape to accommodate unidirectional seated reception of the infusion pump 12. In this regard, as shown in the exemplary drawings (FIGS. 1 and 4), the pocket 16 is depicted with a generally upwardly open and rectangular shape for close-fitting reception of the infusion pump 12, with an aperture 34 formed at an upper right corner of the pocket 16 (FIGS. 1 and 2) for seated reception of the luer fitting 22.

An optical communications interface is provided for data transmission between the infusion pump 12 and the communication station 14, when the pump is seated within the station pocket 16. More particularly, as shown best in FIGS. 2 and 5, a bottom wall 36 of the station pocket 16 includes a pair of relatively small optical lenses 38 and 40 which respectively overlie a light emitting device 42 and a light detecting device 44 mounted within the station housing 32 (FIG. 5). These optical devices 42 and 44 are electrically coupled with an internal station controller 46 (FIG. 5) for respectively transmitting and receiving optically encoded data, as will be described in more detail.

Although the specific construction of the optical devices 42, 44 may vary, one preferred light emitting device comprises an infrared light emitting diode (L.E.D.) available, for example, from Siemens Components, Inc., Optoelectronics Division of Cupertino, Calif., under Model designation SFH, 405 Series, and shown connected in series with a field effect transistor. Similarly, a suitable light detecting device 44 is available in the form of a phototransistor from the same vendor, under Model designation SFH, 305 Series.

Counterpart optical communication devices are also mounted within the pump case 18 in respective association with a pair of lenses 48 and 50 mounted on a rear panel 52 (FIG. 3) of the pump case. More particularly, the lens 48 on the case 18 overlies a light detecting device 54 (FIG. 5) such as a phototransistor, whereas the lens 50 overlies a light emitting device 56 such as a light emitting diode (L.E.D.). Suitable optical devices mounted within the pump case 18 may correspond with those previously described with respect to the communication station 14.

Importantly, the light emitting device 42 on the station 14 is positioned for direct optical alignment with the light detecting device 54 on the infusion pump 12, when the pump is seated within the station pocket 16. Similarly, the light detecting device 44 on the station 14 is aligned for optical communication with the light emitting device 56 on the pump 12, when the pump is seated within the station pocket. With this arrangement, two-way data communication via the optical interface is possible between the pump controller 30 and the station controller 46, as viewed in FIG. 5. A protective cover such a paper label 58 or the like (FIG. 3), which is transparent to infrared signal transmission, may be mounted on the pump case 18 to normally conceal the lenses 48, 50 and associated optical elements from view.

In use, the infusion pump 12 is seated within the station pocket 16 when desired for purposes of two-way data transfer, without requiring interruption of normal pump operation. With the pump 12 seated in place, control means such as a key pad having key switches or actuator buttons 60 or the like on the station housing 32 can be appropriately manipulated to initiate a data transfer sequence. The data transfer sequence may also be initiated remotely. A preferred sequence involves substantial handshake transmission and identification information to verify accurate communication. As soon as a satisfactory communication link has been established and verified, the data transfer sequence may include retrieval of stored data within the pump controller 30, such as data relating to medication dispensing events stored in memory within the pump controller.

Retrieved data may be displayed directly on a station display panel 62, or otherwise suitably relayed to the computer terminal 20 which may be internal or remote.

Link-up with a remote computer 20 may be established via a computer cable port 64 and associated data transmission cable connected to the computer 20, or by means of a phone jack 66 (FIGS. 1 and 4) through the use of an internal station modem 68. In either case, the remote computer 20 can be used to receive and display data retrieved from the pump 12.

Further data transmission activities between the pump 12 and communication station 14 may include transmission of programming information to the pump 12, for purposes of regulating future pump operation. Such programming function is particularly useful when the data is received at a remote computer station 20, which may be located in the offices of a medical facility remote from the communication station 14 located, for example, in a patient's residence.

In addition, the communication station 14 can be adapted for other types of data transfer relevant to patient condition and/or medication delivery to the patient. For example, as illustrated in FIGS. 4 and 5, the station housing 32 may be equipped with a glucose sensor unit 70 or the like having a receptacle 72 adapted to receive a glucose sensor test strip or electrode 73 for analyzation.

In this regard, the station may include a built-in sensor unit of the general type available commercially from Miles Inc. of Elkhart, Ind. under the name Glucometer, or from Boehringer Mannheim Corporation of Indianapolis, Ind. under the name Accu-Chek Easy. The inclusion of the glucose sensor unit as part of the station 14 permits glucose data transfer to the computer 20 which may be a remote terminal in a medical facility. In addition, programming data transferred to the pump 12 may be reflective of the glucose reading.

The data transfer system 10 of the present invention thus provides an easy-to-use system for regularly reviewing medication dispensing histories and for reprogramming pump operation, as may be required in accordance with the needs of a particular patient. The two-way data transmission occurs without compromising the integrity of the sealed pump case 18, with the pump and communication station include independent power sources for operating the optoelectronic components. Such data transmission can be accomplished on a remote basis, without requiring regular and frequent patient visits to a medical facility.

Although an exemplary embodiment of the data transfer system 10 of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as being within the scope of the present invention.

What is claimed is:

1. A data transfer system for use with a medication infusion pump having a pump controller for programmable delivery of medication to a patient, said data transfer system comprising:
   data transfer means on an infusion pump for sending and receiving data;
   a communication station including means for removably receiving and supporting the infusion pump in a predetermined position without interrupting operation of the infusion pump to deliver medication to a patient; and
   data transfer means on said station for sending and receiving data, said data transfer means on the pump and on said station being aligned with each other to establish a data transfer interface between the pump controller and said station when the pump is supported by said station in said predetermined position.

2. A data transfer system as defined in claim 1, wherein said data transfer means on the pump and said data transfer means on said station, when aligned, establish an optical data transfer interface.

3. A data transfer system as defined in claim 1, wherein said means for receiving and supporting the pump comprises a station housing shaped to define a pocket for receiving and supporting the pump in said predetermined position.

4. A data transfer system as defined in claim 1, wherein said station includes control means for initiating data transfer between said station and the pump, controller via said interface.

5. A data transfer system as defined in claim 1, wherein said station includes display means for displaying data transmitted via said interface from the pump controller to said station.

6. A data transfer system as defined in claim 1, further including means for programming the pump controller by data transfer to the pump via said interface.

7. A data transfer station as defined in claim 1, further including a sensor on said station for generating a signal representative of a patient parameter, said data transfer means being responsive to said signal to send programming data to said pump controller.

8. A data transfer station as defined in claim 7 wherein said sensor comprises a glucose sensor.

9. A data transfer system for use with a medication infusion pump having a pump controller for programmable delivery of medication to a patient, said data transfer system comprising:
   data transfer means on an infusion pump for sending and receiving data;
   a communication station including means for removably receiving and supporting the infusion pump in a predetermined position; and
   data transfer means on said station for sending and receiving data, said data transfer means on the pump and on said station being aligned with each other to establish a data transfer interface between the pump controller and said station when the pump is supported by said station in said predetermined position;
   said data transfer means on the pump comprising a light emitting device and a light detecting device, and further wherein said data transfer means of said station comprises a light emitting device and a light detecting device, said light emitting device on the pump being aligned with said light detecting device on said station, and said light detecting device on the pump being aligned with said light emitting device on said station, when the pump is supported on said station in said predetermined position.

10. A data transfer system for use with a medication infusion pump having a pump controller for programmable delivery of medication to a patient, said data transfer system comprising:
   data transfer means on an infusion pump for sending and receiving data;

a communication station including means for removably receiving and supporting the infusion pump in a predetermined position; and data transfer means on said station for sending and receiving data, said data transfer means on the pump and on said station being aligned with each other to establish a data transfer interface between the pump controller and said station when the pump is supported by said station in said predetermined position;

said station including means for transferring data between said station and a remote terminal, whereby said station comprises a data relay link between said remote terminal and the pump controller;

said means for transferring data between said station and a remote terminal comprising a computer cable port.

11. A data transfer system for use with a medication infusion pump having a pump controller for programmable delivery of medication to a patient, said data transfer system comprising:

data transfer means on an infusion pump for sending and receiving data;

a communication station including means for removably receiving and supporting the infusion pump in a predetermined position; and data transfer means on said station for sending and receiving data, said data transfer means on the pump and on said station being aligned with each other to establish a data transfer interface between the pump controller and said station when the pump is supported by said station in said predetermined position;

said station includes means for transferring data between said station and a remote terminal, whereby said station comprises a data relay link between said remote terminal and the pump controller;

said means for transferring data between said station and a remote terminal comprising a modem.

12. A medication infusion pump, comprising:

a pump housing;

means within said pump housing for programmable delivery of medication to a patient and for storing data representative thereof; and optoelectronic data transfer means carried by said pump housing for sending and receiving data between said pump housing and an external data device without interrupting programmable delivery of medication to a patient.

13. A medication infusion pump as defined in claim 11, wherein said optoelectronic data transfer means comprises infrared emission and detection means, said pump further including a cover mounted over said optoelectronic data transfer means, said cover being substantially transparent to infrared signals.

14. A communication station for two-way data transmission with a medication infusion pump controller, comprising:

a station housing having means for removably receiving and supporting an infusion pump controller in a predetermined position;

a glucose sensor on said station housing for generating a signal representative of patient blood glucose level; and data transfer means carried by said station housing for sending and receiving data between said station and the pump controller when said pump controller is supported on said station housing in said predetermined position.

15. A communication station as defined in claim 14, wherein said data transfer means comprises optoelectronic means.

16. A communication station as defined in claim 14, wherein said station includes control means for initiating data transfer between said station and the pump controller.

17. A communication station as defined in claim 14, wherein said station includes display means for displaying data transmitted from the pump controller to said station.

18. A communication station as defined in claim 14, further including means for programming the pump controller by data transfer to the pump controller.

19. A communication station for two-way data transmission with a medication infusion pump controller, comprising:

a station having means for removably receiving and supporting an infusion pump controller in a predetermined position; and data transfer means carried by said station housing for sending and receiving data between said station and the pump controller when said pump controller is supported on said station housing in said predetermined position;

said station including means for transferring data between said station and a remote terminal, whereby said station comprises a data relay link between said remote terminal and the pump controller;

said means for transferring data between said station and a remote terminal comprising a modem.

20. A communication station for two-way data transmission with a medication infusion pump controller, comprising:

a station having means for removably receiving and supporting an infusion pump controller in a predetermined position; and data transfer means carried by said station housing for sending and receiving data between said station and the pump controller when said pump controller is supported on said station housing in said predetermined position;

said station including means for transferring data between said station and a remote terminal, whereby said station comprises a data relay link between said remote terminal and the pump controller;

said means for transferring data between said station and a remote terminal comprising a modem.

21. In combination:

a medication infusion pump having programmable means for scheduled delivery of medication to a patient and for storing data representative thereof;

a communication station having means for removably receiving and supporting said pump in a predetermined position; and optoelectronic data transfer means on said pump and said station to establish a data transfer link therebetween when said pump is supported on said station in said predetermined position and without interrupting operation of the pump to deliver medication to a patient.

* * * * *

UNITED STATES PATENT AND TRADEMARK OFFICE
CERTIFICATE OF CORRECTION

PATENT NO. : 5,376,070

DATED : December 27, 1994

INVENTOR(S) : Richard E. Purvis, et al

It is certified that error appears in the above-identified patent and that said Letters Patent is hereby corrected as shown below:

In claim 19, at column 8, line 35, change "modem" to --computer cable port--.

Signed and Sealed this

Sixteenth Day of May, 1995

Attest:

BRUCE LEHMAN

Attesting Officer

Commissioner of Patents and Trademarks